United States Patent
Walker, Jr. et al.

(10) Patent No.: US 7,297,810 B2
(45) Date of Patent: Nov. 20, 2007

(54) HIGH REFRACTIVE INDEX MONOMERS FOR OPTICAL APPLICATIONS

(75) Inventors: Christopher B. Walker, Jr., St. Paul, MN (US); Roger A. Mader, Stillwater, MN (US); Emily S. Goenner, Shoreview, MN (US); Brant U. Kolb, Afton, MN (US); Sharon Wang, St. Paul, MN (US); Joan M. Noyola, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 485 days.

(21) Appl. No.: 11/026,674

(22) Filed: Dec. 30, 2004

(65) Prior Publication Data

US 2006/0147703 A1    Jul. 6, 2006

(51) Int. Cl.
C07C 69/52    (2006.01)

(52) U.S. Cl. ............... 560/221; 526/292.4; 526/292.5

(58) Field of Classification Search ........... 560/221
See application file for complete search history.

(56) References Cited

U.S. PATENT DOCUMENTS

| | | | |
|---|---|---|---|
| 4,396,476 A | 8/1983 | Roemer et al. | |
| 5,677,050 A | 10/1997 | Bilkadi et al. | |
| 6,005,137 A | 12/1999 | Moore et al. | |
| 6,277,485 B1 | 8/2001 | Invie et al. | |
| 6,376,590 B2 | 4/2002 | Kolb et al. | |
| 6,416,838 B1 | 7/2002 | Arney et al. | |
| 6,653,425 B1 | 11/2003 | Armstrong-Poston et al. | |
| 6,656,258 B2 | 12/2003 | Elsbernd et al. | |
| 6,660,388 B2 | 12/2003 | Liu et al. | |
| 6,663,978 B1 | 12/2003 | Olson et al. | |
| 6,677,028 B1 | 1/2004 | Lasch et al. | |
| 6,680,125 B1 | 1/2004 | Sasaki | |
| 6,706,403 B1 | 3/2004 | Olofson et al. | |
| 6,716,891 B1 | 4/2004 | Meisenburg et al. | |
| 6,760,157 B1 | 7/2004 | Allen et al. | |
| 6,777,070 B1 | 8/2004 | Murata et al. | |
| 6,778,753 B2 | 8/2004 | Blomquist | |
| 6,788,463 B2 | 9/2004 | Merrill et al. | |
| 6,800,378 B2 | 10/2004 | Hawa et al. | |
| 6,818,680 B2 | 11/2004 | Shustack | |
| 2002/0001710 A1 | 1/2002 | Kang et al. | |
| 2002/0123589 A1 | 9/2002 | Olson et al. | |
| 2003/0105189 A1 | 6/2003 | Yashiro et al. | |
| 2003/0224250 A1 | 12/2003 | Setthachayanon et al. | |
| 2005/0136252 A1 | 6/2005 | Chisholm et al. | |

FOREIGN PATENT DOCUMENTS

| | | |
|---|---|---|
| EP | 0339880 | 8/1993 |
| EP | 1014113 | 6/2000 |
| JP | 05215902 | 8/1993 |
| JP | 08034768 | 2/1996 |
| JP | 2002-293762 | 10/2002 |
| WO | WO 2006/007286 | 1/2006 |

OTHER PUBLICATIONS

Park, Jong Hyeok et al., White Emission From Polymer/Quantum Dot Ternary Nanocomposites by Incomplete Energy Transfer, NANOTECHNOLOGY, vol. 15, No. 9, Sep. 2004, pp. 1217-1220.

Primary Examiner—Bernard Lipman
(74) Attorney, Agent, or Firm—Carolyn A. Fischer

(57) ABSTRACT

The present invention includes optical coatings containing ultraviolet curable monomers employing a bromine substituted fluorene structure. The fluorene backbone of the monomers of the present invention may also be functionalized with one or more polymerizable or reactive functionalities, and most readily at the 9 position. Compositions of the present invention include the reactive bromosubstituted fluorenes combined with inorganic nanoparticles, particularly nanoparticles with reactive surface modifiers exhibiting polymerizable functionality. Reactive high index nanoparticles such as surface modified zirconia are contemplated.

4 Claims, 3 Drawing Sheets

HIGH REFRACTIVE INDEX MONOMERS FOR OPTICAL APPLICATIONS

BACKGROUND OF THE INVENTION

The development of films or coatings as protective films for display devices such as a CRT screen is well documented in the art. These include antireflective coatings, hardcoats, optical coatings, and the like. Nevertheless, there continues to be a need for further improvement in the development of polymerizable high index materials for optical applications. Exemplary applications include antireflective coatings, hardcoats, and brightness enhancement film materials. Many polymerizable films have a refractive index of 1.5 or less. Because of the optical advantages, however, an increase of the refractive index to 1.58 or more would be a desirable improvement. Furthermore, there is a need for durable, inexpensive, and yet high quality antireflective coatings that exhibit a relatively low reflectance, that is less than 1%.

SUMMARY OF THE INVENTION

The above-referenced concerns are resolved by the development of new ultraviolet curable monomers employing a substituted fluorene structure. Bromine is readily substituted at the 2 position in the mono brominated derivative, the 2 and 7 positions in the dibrominated derivative and the 2, 3, and 7 positions in the tribrominated derivative. The fluorene backbone of the monomers of the present invention may also be functionalized with one or more polymerizable or reactive functionalities, and most readily at the 9 position. In particular, preferred embodiments incorporate reactive, pendant acrylate groups.

Compositions of the present invention include the reactive bromosubstituted fluorenes combined with inorganic nanoparticles, particularly nanoparticles with reactive surface modifiers exhibiting polymerizable functionality. Reactive high index nanoparticles such as zirconia are preferred, although other high index nanoparticles such as titania are acceptable. Photoinitiators may also be employed in the present compositions thereby enhancing free radical curing by ultraviolet light for example.

One advantage of the monomers of the present invention is the copolymerizability and high refractive index of the monomers. A second advantage is the compatibility of the monomers with the solvents employed in dispersing functionalized nanoparticles thereby forming stable coating formulations. Another advantage of the high refractive index monomers is that antireflective coatings including the high refractive index monomers within high index optical layer(s) may be provided, thereby enhancing the optical properties of the antireflective coating.

DETAILED DESCRIPTION

Figure 2:
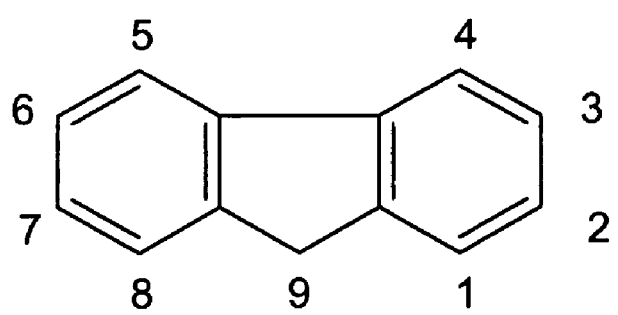
FIG. 2 illustrates a fluorene structure and the nine positions referred to throughout the specification.

The present invention includes the development of bromosubstituted fluorenes as a coating matrix. The incorporation of bromine is believed to raise the refractive index and is readily substituted at the 2 position in the mono brominated derivative, the 2 and 7 positions in the dibrominated derivative and the 2, 3, and 7 positions in the tribrominated derivative. The substituted polymers are also functionalized with one or more polymerizable functionalities along the fluorene backbone, and preferably at the 9 position. FIG. 2 illustrates a fluorene structure that may be substituted about the positions shown. The functional groups particularly emphasized include reactive, pendant acrylate groups. Co-polymers may be made from other acrylates and methacrylates, and from monofunctional derivatives represented by the generic structure shown below. Pendant acrylate groups include those selected from the group of acrylate, methacrylate, polyacrylate, polymethacrylate, and polymethylmethacrylate compounds formed from acrylic acid, methacrylic acid, trimethoxysilylpropylmethacrylate, and trimethoxysilylpropylacrylate, for example.

The use of the new monomers of the invention are envisioned in combination with other monomers, multifunctional acrylates, crosslinking monomers, fillers, nanoparticles, adhesion promoters, slip agents, initiators, photoinitiators, dyes, and solvents, and are given in weight percent ranges relative to the total weight of the optical coating composition. The weight percents of each constituent are given relative to the total weight of the compositions, absent the solvent used in the processing thereof. For UV curable formulations, the photoinitiators may be employed between 0.05% and 10%, although preferably between 1-4%. For the films of the invention, the nanoparticles were provided at 20-60 wt % and even more preferably in a range of 30-38.5 wt %, whereby the weight percents given reflect the weight of nanoparticles not yet surface modified. In accordance with the present invention, the nanoparticle surface modifier weight percent ratio preferably ranges from about 2.70:1 to 6:1. Stated another way, the weight percent range for nanoparticles with surface modifiers is the sum of the two. To illustrate, example 12 has 30% ZrO2+11.1% surface modifier, so that the weight percent of the surface modified particles is 41.1%. Similarly, example 16 exhibits a 35.32% wt % of surface modified nanoparticles, wherein the wt % is also relative to the total compositional weight. Table 1 below gives exemplary nanoparticle/surface modifier combinations of the present invention.

TABLE 1

| Wt % ZrO2 | Wt % SM at 2.70:1 nano:SM | Total wt % at 2.70:1 nano:SM | Wt % SM at 6:1 nano:SM | Total wt % at 6:1 nano:SM |
|---|---|---|---|---|
| 20 | 7.41 | 27.41 | 3.33 | 23.33 |
| 30 | 11.11 | 41.11 | 5 | 36 |
| 38.5 | 14.26 | 52.76 | 6.42 | 44.92 |
| 60 | 22.22 | 82.22 | 10 | 70 |

The bromosubstituted monomers of the invention were generally provided at about 25-60 wt % and more preferably at about 31-58 wt %. The multifunctional acrylates or crosslinkers are generally provided at about 25-50 wt %.

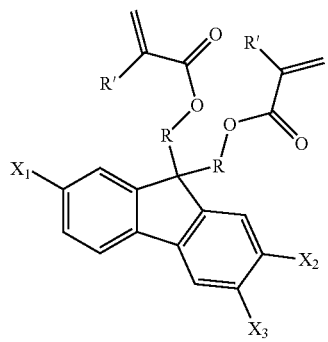

Structure I

X1 = Br
X2 = H or Br
X3 = H or Br (only when X2 = Br)
R = alkylene or alkylene oxy (up to 8 atoms)
R' = H or methyl

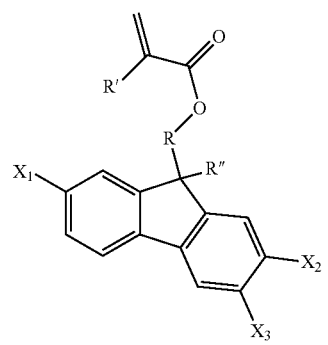

Structure II

Figure 3:
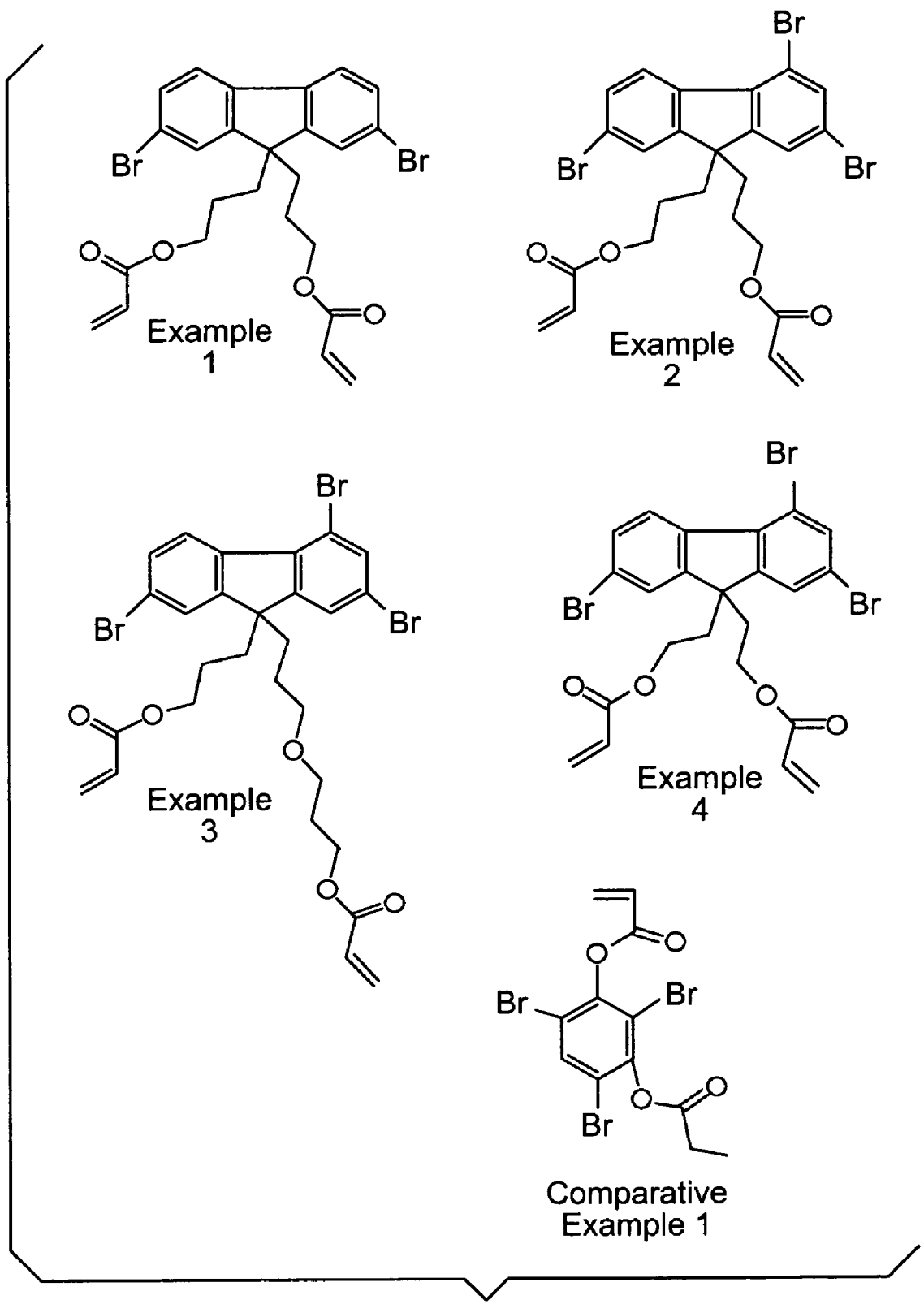
FIG. 3 illustrates the structures of Examples 1-4 and Comparative Example 1.

X1 = Br
X2 = H or Br
X3 = H or Br (only when X2 = Br)
R = alkylene or alkylene oxy (up to 8 atoms)
R' = H or methyl
R'' = H or alkyl Two classes of bromo-substituted fluorene monomers are characterized by the structures illustrated above. Examples 1-4, illustrated in FIG. 3, exemplify molecules that may be formed as given above. As such, a preferred group of bromo substituted fluorene monomers may be selected from the group including acrylic acid 3-[9-(3-acryloyloxy-propyl)-2,3,7-tribromo-9H-fluoren-9-yl]-propyl ester, acrylic acid 3-{9-[3-acyloyloxy-propoxy)-propyl]-2,3,7-tribromo-9H-fluoren-9-yl}-propyl ester, 3-[9-(3-acryloyloxy-propyl)-2,7-dibromo-9H-fluoren-9-yl]-propyl ester, and 2-[9-(2-acryloyloxy-ethyl)-2,7-dibromo-9H-fluoren-9-yl]-ethyl ester. It has been found that the bromosubstituted monomers of the present invention as exemplified by this preferred group, possess a high refractive index (greater than or about 1.58 to 1.6), good solubility, good miscibility with the nanoparticles, and reasonable durability after curing, especially when formulated with zirconia nanoparticles.

Polymerizable compositions of the present invention incorporating the bromosubstituted fluorene described above may be characterized as nanocomposites. Nanocomposites are defined as a polymer matrix that contains well-dispersed nanoparticles. Nanoparticles are defined as particles that are smaller than 100 nanometers. U.S. Pat. No. 5,385,776 exemplifies the current understanding of nanocomposites incorporated within polyamides and is herein incorporated by reference. A nanoparticle is generally an inorganic particle such as a metal, metal oxide, metal nitride, metal carbide or metal chloride. In accordance with the present invention, the use of high index nanoparticles increases the refractive index of compositions incorporating the same. Preferred nanoparticles include crystalline zirconia, although other high index nanoparticles such as titania, antimony, mixtures of metal oxides, and mixed metal oxides are acceptable. Crystalline zirconia is preferred over amorphous zirconia due to the greater refractive index of compositions containing crystalline zirconia. Functionalized silica nanoparticles may be used for added reinforcement, although it lowers the refractive index of the cured coating. Examples of useful zirconia are those described in U.S. Pat. No. 6,376,590, and examples of titania are described in U.S. Pat. No. 6,432,526, both incorporated by reference in their entirety.

Surface modification of the nanoparticles relates to the reaction of specific molecules on the surface of particles, and is useful in achieving good dispersion within the polymer matrix. Accordingly, the nanoparticles are preferably treated with surface modifying agents such as carboxylic acids, silanes and/or dispersants to help compatibilize them with the polymer matrix. U.S. Pat. No. 6,329,058 exemplifies typical surface modifiers and is herein incorporated by reference. In essence, it is believed that surface modification prevents particle agglomeration thereby facilitating particle dispersion within the monomers and resins, and therefore enhancing the transparency of the coating. Preferred surface modifiers are carboxylic acids and silanes including methoxyethoxyethoxyacetic acid (MEEAA) and A1230 (a polyethersilane or PEG-silane). The use of surface modifiers with high refractive index is also preferred and includes naphthyl acetic acid and trimethoxy phenyl silane.

The nanoparticles of the present invention may also be surface modified by reactive surface modifiers. Reactive surface modification means that surface modifiers are employed that include functional groups that facilitate polymerization in addition to functionality that can either adsorb or covalently bond with the particle surface. When a coating of the present invention is polymerized (or cured), it forms a nanocomposite having particles covalently linked to the polymer matrix. When employing mixtures of nanoparticles, a combination of benefits may be realized. For example, surface modified zirconia may be added to raise the refractive index, while surface modified silica may be added to further enhance durability.

Compositions of the present invention may further contain any of the well known Type I and Type II UV photoinitiators, such as the substituted acetophenones, benzoins, phosphine oxides, benzophenone/amine combinations, and other photoinitiator classes well known to those in the art. Exemplary photoinitiators include Irgacure™ 819, Darocure™ 1173, or TPO supplied for example by Ciba Geigy of Tarrytown, N.Y. It is believed that radical photoinitiators cleave in the presence of ultraviolet light to form radicals that initiate the polymerization of the acrylate and methacrylate functional groups in the formulation to form the crosslinked nanocomposite. Known types and classes of radical photoinitiators may be employed as described in, "Chemistry and Technology of UV & EB Formulation For Coatings, Inks, & Paints" of Volume 3 of Photoinitiators for Free Radical Cationic Polymerization, published by SITA Technology Ltd., Gardiner House, Broomhill Road, LONDON SW18184JQ ENGLAND, herein incorporated by reference.

Specific photoinitiators which are useful in the compositions of the invention include onium salts as described in U.S. Pat. No. 5,545,676, herein incorporated by reference. Onium salts have been found to be useful as coinitiators in high speed visible light curing of free radically polymerizable systems. Photoinitiators are typically employed from about 0.05 wt % to about 10 wt %, and more preferably at about 1 to 4 wt %.

The invention is further illustrated, but not thereby limited, by the Examples given below. In particular, the examples given provide a template for production of a class of compounds characterized as bromo-substituted fluorene monomers, and also polymerizable compositions containing the same.

EXAMPLE 1

Preparation of Acrylic Acid 3-[9-(acryloyloxy-propyl)-2,7-dibromo-9H-fluoren-9-yl]-propyl ester (DBFDA): There are various suppliers that are known in the art that may provide the various chemical constituents of the present invention. Because of the availability, as known to one of ordinary skill, further discussion is abbreviated. Aldrich Chemical Co. of Milwaukee, Wis. exemplifies one of many known chemical suppliers.

A mixture containing 47 grams of 2,7-dibromofluorene, provided by Alfa Aesar for example, 3.3 grams of benzyl-triethylammonium chloride, and 29 grams of 50% aqueous sodium hydroxide in 470 ml of dimethylsulfoxide was stirred and to it was added 50.8 grams of 3-bromo-1-propanol, provided by Aldrich Chemical for example. An exothermic reaction occurred and the temperature was controlled at 50° C. by means of an ice bath. After the exothermic reaction was complete the mixture was maintained at 35° C. for one hour and then cooled to 23° C. and added to 200 ml of water. The solid obtained was recrystallized from methanol/water to give a crude material which was further purified by recrystallization from ethyl acetate/hexane to yield 23.5 grams of 3-[2,7-Dibromo-9-(3-hydroxypropyl)-9H-fluorene-9-yl]-propane-1-ol.

A solution containing 15 grams of 3-[2,7-Dibromo-9-(3-hydroxypropyl)-9H-fluorene-9-yl]-propane-1-ol and 18.7 grams of diisopropylethylamine in 150 ml of tetrahydrofuran was cooled to 10° C., and to it was slowly added a solution of 7.7 grams of acryloyl chloride in 18 ml of tetrahydrofuran. The temperature was maintained at 10° C. during the addition. After stirring at 10° C. for one hour the mixture was poured into a mixture containing 100 ml of 2% aqueous HCl and 100 ml of ethyl acetate. The organic phase was separated and dried over anhydrous sodium sulfate. The solvent was removed and the residue purified by column chromatography on silica gel eluted with 15% ethyl acetate in hexane to give 8.5 grams of acrylic acid 3-[9-(acryloyloxy-propyl)-2,7-dibromo-9H-fluoren-9-yl]-propyl ester. This product was verified by NMR analysis to be present and pure.

EXAMPLE 2

Preparation of Acrylic acid 2-[9-(2-acryloyloxy-ethyl)-2,7-dibromo-9H-fluoren-9-yl]-ethyl ester(4) (DBFDC2A)

A solution containing 50 grams of 2-bromoethanol (Aldrich) and 0.1 gram of p-toluene sulfonic acid was stirred and to it was added slowly with cooling 33.6 grams of dihydropyran. After the addition was complete the mixture was cooled to room temperature. This gave the tetrahydopyranyl ether of 2-bromoethanol which was used without further purification.

A mixture containing 5.0 grams of 2,7-dibromofluorene, 3.1 grams of sodium hydroxide and 0.35 grams of Benzyl-triethylammonium chloride in 50 ml of dimethylsulfoxide was stirred and to it was added 9.7 grams of the tetrahydropyranyl ether of 2-bromoethanol. The temperature rose slowly to 50° C. The temperature was maintained at 35° C. for 1 hr after which the mixture was added to 100 ml of water and 50 ml of ethyl acetate and 50 ml hexane. The organic layer was removed washed 2x with 100 ml of water and dried over sodium sulfate. The solvent was removed and 150 ml of ethanol added followed by 0.5 grams p-toluene sulfonic acid. The mixture was stirred at 70° C. for 30 min. The mixture was cooled and treated with aqueous potassium carbonate to ~pH8. The solvent was removed and the residue treated with 50 ml of 1;1 ethyl acetate:hexane and 25 ml of water the solid was filtered and washed with water. Recrystallization from 1:1 ethyl acetate hexane to give 4.5 grams of 2-[2,7-dibromo-9-(2-hydroxy-ethyl)-9H-fluoren-9-yl]-ethanol which was esterified by the process described in example 1 to give 3.8 grams of Acrylic acid 2-[9-(2-acryloyloxy-ethyl)-2,7-dibromo-9H-fluoren-9-yl]-ethyl ester(4). This product was verified by NMR analysis to be present and pure.

EXAMPLE 3

Preparation of acrylic acid 3-{9-[3-(3-acryloyloxy-propoxy)-propyl}-2,3,7-tribromo-9H-fluoren-9-yl}-propyl ester(3) (WTBFDA)

A mixture containing 60 grams of fluorene and 1.17 grams of ferric chloride in 700 ml of chloroform was stirred at 25° C. and to it was slowly added 173 grams of bromine. The temperature rose to 24° C. during the addition. After the addition was complete the mixture was stirred for 30 minutes then 500 ml of water added. The solid was filtered and washed with acetone. After drying overnight the solid was slurried in 600 ml of acetone at reflux then cooled and filtered to give 110 grams of 2,3,7-tribromofluorene.

A mixture containing 40 grams of 2,3,7-tribromofluorene, 19.9 grams of sodium hydroxide and 2.3 grams of benzyl-triethylammonium chloride in 400 ml of dimethylsulfoxide were stirred and to it was added 51.4 grams of 3-bromo-1-propanol in increments. The temperature rose slowly to 30

C. The temperature was maintained at 30 C for one hour after which the mixture was added to 500 ml of water. The mixture was extracted with 500 ml of ethyl acetate. The organic phase was washed three times with 300 ml of water. After drying over sodium sulfate the solvent was removed giving a crude product which was purified by column chromatography on silica gel eluted first with 1:1 ethyl acetate: hexane followed by 3:2 ethyl acetate hexane and finally ethyl acetate. This gave 13 grams of 3-{2,3,7-tribromo-9-[3-(3-hydroxy-propoxy)-propyl]-9H-flouren-9-yl}-propan-1-ol in the second fraction. A 10.1 gram sample of this was esterified by the process described in example 1 to give 6.4 grams of acrylic acid 3-{9-[3-(3-acryloyloxy-propoxy)-propyl}-2,3,7-tribromo-9H-fluoren-9-yl]-propyl ester(3). This product was verified by NMR analysis to be present and pure.

EXAMPLE 4

Preparation of 3-[9-(3-acryloyloxy-propyl)-2,3,7-tribromo-9H-fluoren-9-yl]-propyl ester(2) (TBFDA)

A mixture containing 30 grams of 2,3,7-tribromofluorene, 1.7 grams of benzyltriethylammonium chloride, and 14.9 gram of sodium hydroxide in 300 ml of dimethylsulfoxide was stirred and to it was added 26.1 grams of 3-bromo-1-propanol. The temperature rose slowly to 50 C, was allowed to cool to 35° C. and was maintained at 35 C for one hour after which the mixture was added to 200 ml of water. The solid which formed was filtered and recrystallized from methanol/water to give 25 grams of solid. After drying this was recrystallized from ethyl acetate/ hexane to give 14.4 grams of 3-[2,3,7-tribromo-9-(3-hydroxy-propyl)-9H-fluoren-9-yl]-propan-1-ol. A 7.6 grams sample of this material was esterified using the procedure described in example 1 to give 4.2 grams of 3-[9-(3-acryloyloxy-propyl)-2,3,7-tribromo-9H-fluoren-9-yl]-propyl ester(2). This product was verified by NMR analysis to be present and pure.

Examples 1-4 provide a basic template of the formation of the bromo-substituted monomers in accordance with the present invention.

EXAMPLE 5

Surface Modification of Zirconia Nanoparticles

The following exemplifies surface modification of any suitable nanoparticle and in particular relates to the preparation of a silane-modified zirconia nanoparticle dispersion. 400.0 grams of Nalco™ zirconia sol and 26.57 grams of MEEAA (Sigma-Aldrich, Milwaukee, Wis.) were charged to a 1 L round bottom flask. The water and acetic acid were removed via rotary evaporation at 80° C. The powder thus obtained was redispersed in 398 grams of D.I. water. 416.56 grams of the particles dispersed in water was charged to a 2 L beaker. While stirring the particle dispersion, 800 grams of 1-methoxy-2-propanol, 45.0 grams of Silane A-174™, and 29.21 grams of Silquest A-1230™, supplied for example by OSI Specialties, a Crompton Corporation, of Greenwich, Conn. This mixture was slowly added to the beaker. This mixture was then poured into two quart-sized jars, sealed and heated to 90° C. for three hours. The contents of the jars were removed and concentrated via rotary evaporation to 40.43 wt % zirconia. 1268.0 grams of deionized water and 42.0 grams concentrated aqueous ammonia (29% ammonia) were charged to a 4 L beaker. The concentrated dispersion was added slowly to the beaker while stirring. The white precipitate thus obtained was isolated via vacuum filtration and washed with additional deionized water. The damp solids were dispersed in methylethylketone (MEK). The resultant silane modified zirconia dispersion contained 14.89% zirconia. U.S. Pat. No. 6,800,378, herein incorporated by reference, further describes other inorganic oxide particles useful as nanoparticles, and, aqueous, organic, and mixed sols that may be employed when surface modifying the nanoparticles of the present invention. Mixed oxides containing more than one type of inorganic atom may also be employed as described in U.S. patent application No. US2003 0165680, herein incorporated by reference. Accordingly, in some embodiments, Ti/Sb mixed oxide nanoparticles may be combined with additional nanoparticles having a different elemental composition (e.g., silica, zirconia, alumina, titania, antimony pentoxide). Desirably, such additional nanoparticles, if present, have an average particle size comparable to that of the Ti/Sb mixed oxide nanoparticles. Such nanoparticles may be commercially obtained, for example, from Nalco Chemical Co. (Naperville, Ill.) or Nyacol Nano Technologies, Inc. (Ashland, Mass.). Exemplary additional nanoparticles are also described in U.S. Pat. Nos. 5,037,579; and 6,261,700; which disclosures are incorporated herein by reference.

EXAMPLES 6-10

To develop a solvent-based system, solubility studies were conducted. Examples 1-4 and Comparative Example 1 were solubilized as indicated in Table 2 given below and are respectively identified as Examples 6-10. As shown, each monomer was soluble in one or more of the commonly employed solvents (MEK, acetone, toluene, and ethyl acetate). The comparative example was not soluble in these acceptable solvents. The comparative example is, however, soluble in methylene chloride, but is not considered useful given the hazardous nature of methylene chloride.

TABLE 2

| Example | State | R.I. | Solubility |
|---|---|---|---|
| (Ex. 1 monomer) | Solid | 1.615 | MEK, Acetone, Toluene, Ethyl Acetate |
| (Ex. 4 monomer) | Solid | 1.6237 | Ethyl Acetate, Acetone, MEK |
| (Ex. 3 monomer) | Liquid | 1.5802 | MEK, Acetone, Toluene, Ethyl Acetate |
| (Ex. 2 monomer) | Solid | 1.6198 | MEK, Ethyl Acetate |
| 10 (Comp. Ex. 1) | Solid | | $CH_2Cl_2$ |

Example 1 = DBFDA
Example 2 = DBFDC2A
Example 3 = WTBFDA
Example 4 = DBFDC2A
SR399 = dipentaerythritolpentaacrylate from Sartomer, Exton, PA.

EXAMPLES 11-12

UV curable formulations identified below as Examples 11 and 12 in the table below, were prepared by mixing the solution of surface modified zirconia nanoparticles with acrylate functionalized fluorene (DBFDA, Example 1), a photoinitiator (Irgacure 819, provided by Ciba Specialty Chemicals, Tarreytown, N.Y.), and optionally SR295, a mixture of pentaerythritol tri and tetracrylates available from SARTOMER of Exton, Pa. were prepared as shown in Table 3. The zirconia employed in both examples 11 and 12 is described in Example 5. MEK was added to the formulations until the % solids was 5%.

TABLE 3

|  | NP | wt % ZrO2 | S.M. | wt % S.M. | Wt % resin | Resin(s) | P.I. |
|---|---|---|---|---|---|---|---|
| Ex. 11 | Nalco ZrO2 | 30.0 | 3:1 A174:A1230 | 11.1 | 57.9 | DBFDA | 1.0% 819 |
| Ex. 12 | Nalco ZrO2 | 30.0 | 3:1 A174:A1230 | 11.1 | 57.9 | 50:50 DBFDA:SR295 | 1.0% 819 |

Examples 11 and 12 (as 5% solids, 95% MEK), were coated, dried, and UV cured with a Fusion Systems UV source (employing a "D" bulb) to a nominally 80 nm thickness on a 5 um film of 906 hardcoat on top of a polyester substrate. Example 3 of U.S. Pat. No. 6,299,799, herein incorporated by reference in its entirety, describes an exemplary hardcoat employed in the present invention. First surface reflection measurements were obtained using an MPC 3100 spectrophotometer in accordance with standardized testing method, First Surface Total and CP Reflection Measurement Using the Shimadzu Spectrophotometer. The thickness of the single high index optical layer on 906 hardcoated PET can be calculated from the following relationship:

$$t = \lambda/4\eta$$

where:
t=thickness (nm)
λ=wavelength (nm)
η=refractive index

Ideally, the samples will reflect maximally at 550 nm. The higher reflection at the peak of Example 11 v. Example 12 occurs due to the addition of the low refractive index multifunctional acrylate PETA in Example 12. Tables 3 and 4 given below illustrate coated and cured samples, UV-VIS measurement correlating to thickness, and the abrasion resistance results to date. The cured samples were evaluated for durability through:

Rubbing with cheesecloth using 2 kg weight on top of 6 mm wide "stylus".
Linear scratch testing—with 100 g and 750 g styli.
Cheesecloth testing with 1" diameter pin and 1018 kg weight—

Refractive indices were calculated on the basis of a volume average of the RI of the individual components. The refractive index of neat liquid materials was measured on a Zeiss refractometer. Solids were melted and then measured promptly. Refractive index of a coating is often found to increase 0.01-0.02 after UV curing, as a consequence of increasing coating density.

TABLE 4

| | Fusion Lamp | Solution | Calc. R.I. uncured Sample | nominal thickness | max. in UV/VIS | % R at peak |
|---|---|---|---|---|---|---|
| Ex. 11 | D | 5% MEK | 1.639 | 80 | 560 | 8.49% |
| Ex. 12 | D | 5% MEK | 1.589 | 80 | 560 | 7.84% |

The UV data shows that the target thicknesses were reached, as the reflection is centered near 550 nm, the middle of the visible spectrum. The high % reflection, confirms the high refractive index nature of the coatings.

TABLE 5

| Example | nano | Wt % Nanos | SM | Wt % SM | Wt % R | Resins and ratios | calc RI | Solvent |
|---|---|---|---|---|---|---|---|---|
| Ex 11 | Nalco ZrO2 | 30 | 3:1 A174:A1230 | 11.1 | 57.9 | DBFDA | 1.639 | 5% MEK |
| Ex 12 | Nalco ZrO2 | 30 | 3:1 A174:A1230 | 11.1 | 57.9 | 50:50 DBFDA:SR295 | 1.589 | 5% MEK |
| Ex 13 | Nalco ZrO2 | 29.99 | 3:1 A174:A1230 | 11.09 | 57.92 | 28.96:28.96 DBFDA, SR295 | 1.585 | 5% in Acetone |
| Ex 14 | Nalco ZrO2 | 29.99 | 3:1 A174:A1230 | 11.09 | 57.92 | 28.96:28.96 DBFDA, SR399 | 1.587 | 5% in Acetone |
| Ex 15 | 3M ZrO2 | 30 | 3:1 A174:A1230 | 5.32 | 63.68 | 31.84:31.84 TBFDA:SR399 | 1.596 | 7.5% in acetone |
| Ex 16 | 3M ZrO2 | 30 | 3:1 A174:A1230 | 5.32 | 63.68 | 31.84:31.84 DBFDC2A:SR399 | 1.596 | 7.5% in acetone |
| Ex 17 | | | | | 99 | 50:50 TBFDA:S399 | 1.551 | 7.5% in MEK |

Each of the compositions of Examples 11-17 include 1 wt-% "Irgacure 819" photoinitiator.

Table of Examples 11, 12 and 13-17.

Examples 13-17 were prepared in the same way as examples 11 and 12 with the same surface modified zirconia and resins, and at the wt % ranges and with the solvent listed in the table. It should be emphasized that although the refractive index of Examples 12-16 are below 1.6, when cured, the refractive index of compositions formed in accordance with the present invention generally rises to an index at or above 1.6.

The cured samples were evaluated for durability by mechanically rubbing the sample with a 6 mm "stylus" wrapped with 24 layers of cheesecloth with a 2.2 kg weight onto the stylus (plus the weight of the stylus) and noting how many passes or "rubs" were performed without damage being observed and at how many passes or "rubs" damage was observed. The results are given in an X/Y format, where the number X indicates the number of passes where the sample remained unchanged visually from the abrasion. The number Y represents the point at which damage was observed. Unacceptable abrasion resistance is defined as failure below 25 rubs. The samples are examined at 25, 50, 150, and 200 rubs, but not in between.

| EX. | Nominal thickness apprx thickness | UV-VIS max (nm) UVVIS max | UV lamp UV lamp | Durability Testing 80 nm samples 2 kg/ cheesecloth 2 kg, 6 mm pin cheesecloth | Stylus scratch test/100 g probe linear scratch 100 g, | Stylus scratch test/750 g probe linear scratch 750 g |
|---|---|---|---|---|---|---|
| Ex 11 | 80.00 | 560 | D | 25/50 (5x), 50/100 (1x) | GOOD 0/2 | 2/2 scratched |
| Ex 12 | 80.15 | 480 | D | 50/100, 25/50 (5x) 6 times | GOOD 0/3 | GOOD 0/2 |
| Ex 13 |  | 450 | D | 25/50 |  |  |
| Ex 14 |  | 525 | D | 25/50 (3x), 50/100 |  |  |
| Ex 15 | 86.80 | 600 | D | 25/50 |  |  |
| Ex 16 | 120.00 | 625 | D | 100/150, |  |  |
| Ex 17 | 85.86 | 491 | D | 50/100 |  |  |

It can therefore be concluded that exemplary compositions with acrylate functionalized zirconia and polymerizable resins have achieved durable coating with a refractive index equal to or greater than 1.58. It has been found that compositions of the present invention, as exemplified in the tables when cured will typically exhibit a refractive index of about 1.6 or more.

EXAMPLE 18

Preparation of 3M Zirconia with Surface Modifers (3M $ZrO_2$ 75/25 methacrylaoxypropyltrimethoxy silane/ A1230)

The ZrO2 sol (279.85 g, 40.05% solids, 36.02% ZrO2) was charged to a 1 qt jar. De-ionized water (150 g) was charged with stirring. Methoxypropanol (455 g), Methacryloxypropyl trimethoxy silane (26.33 g) and A1230 (17.8) were charged to a 1 liter beaker with stirring. The methoxypropanol mixture was then charged to the ZrO2 sol with stirring. The jar was sealed and heated to 90 C for 4 hr. After heating the mixture was stripped to 350 g via rotary evaporation. Copending U.S. application Ser. No. 11/027426, filed Dec. 30, 2004, describes exemplary 3M zirconia particles and is hereby incorporated by reference. Nalco and Buhler also provide zirconia particles in accordance with the present invention.

De-ionized water (1287 g) and Concentrated NH3 (28.34, 29wt %) were charged to a 41 t beaker. The above concentrated sol was added to this with minimal stirring. A white precipitate was obtained. The precipitate was isolated as a damp filter cake via vacuum filtration. The damp solids (240 g) were dispersed in methoxypropanol (500 g). The mixture was then concentrated (383 g) via rotary evaporation. Methoxypropanol (220 g) was added and the mixture concentrated (261 g) via rotary evaporation. Methoxypropanol was charged (150 g) and the mixture was concentrated via rotary evaporation. The final product 257 g was isolated at 45.49% solids. The mixture was filtered with a 1 um filter. Methoxypropanol (150 g) was added and the mixture concentrated (363 g ) via rotary evaporation.

Other additives may be included in the present compositions. For example, UV sensitizers, oxygen scavengers, and other components useful in free radical curing may be employed as known in the art.

Films made in accordance with the present invention may be coupled, layered, laminated, and/or otherwise coupled to other films or display devices in accordance with the present invention. U.S. Pat. No. 6,800,378, herein incorporated by reference, describes a process of bonding layers of film together and also of bonding the an antireflective film, for example, upon a display device. The same process may be employed in accordance with the present invention. Known techniques of preparing multilayer films may be employed to include spin coating, knife coating, and the like.

Figure 1:
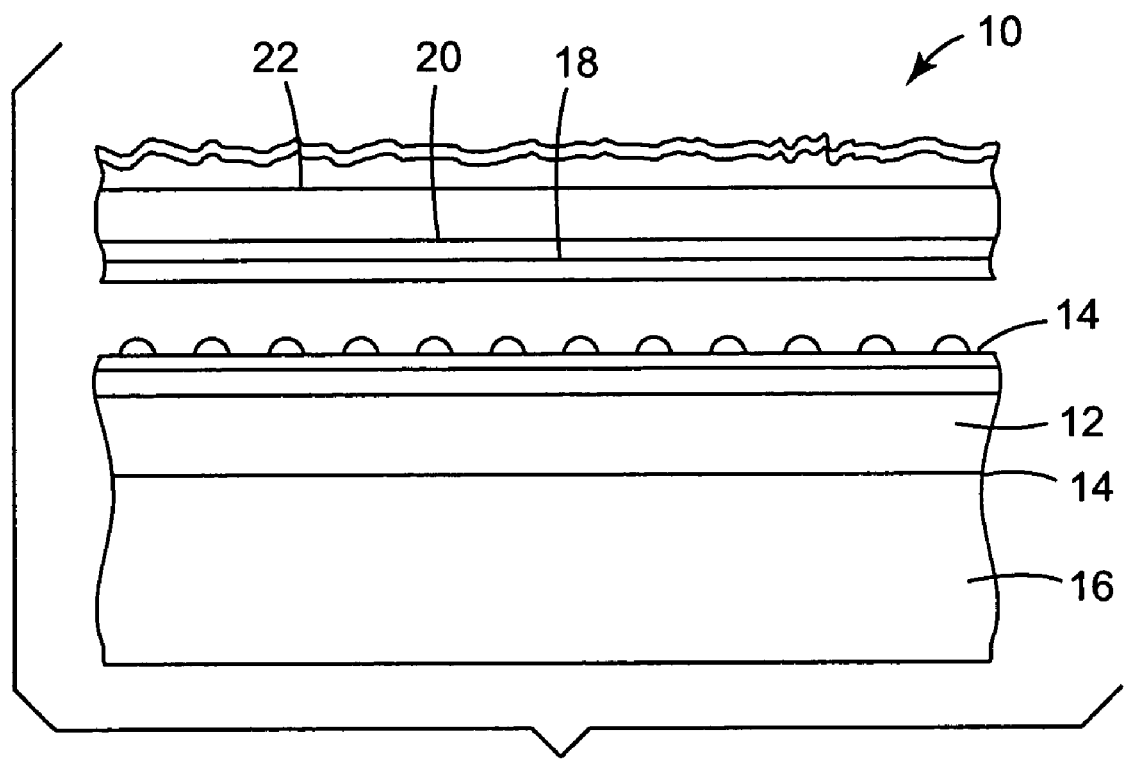
FIG. 1 illustrates an antireflective coating construction containing an optical coating, in accordance with the present invention.
Figure 4:
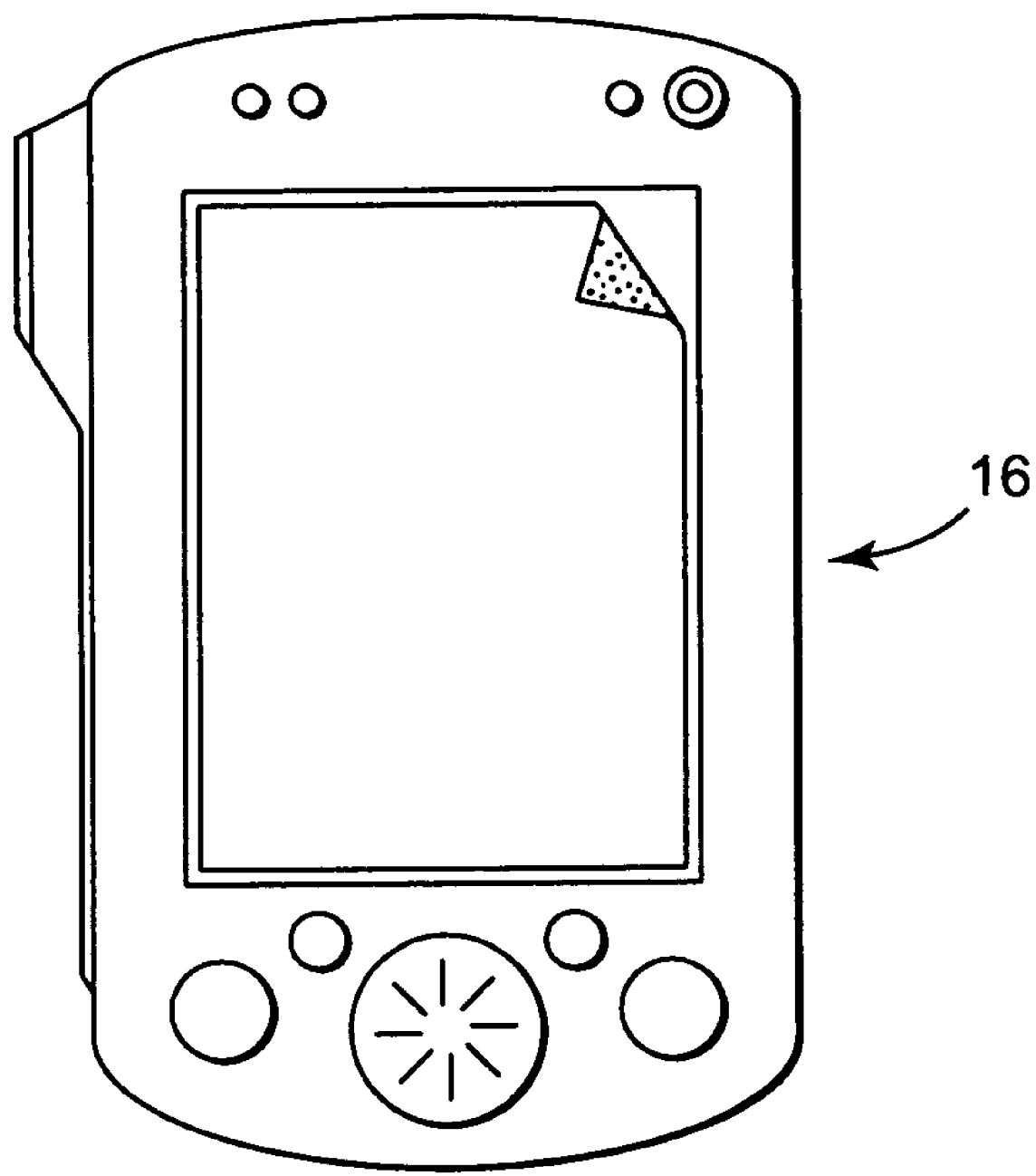
FIG. 4 illustrates a typical display device in accordance with the present invention.
Figure 3:
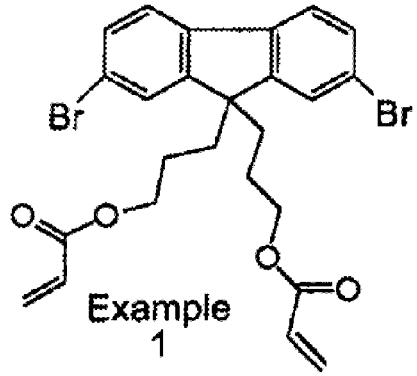
Figure 3:
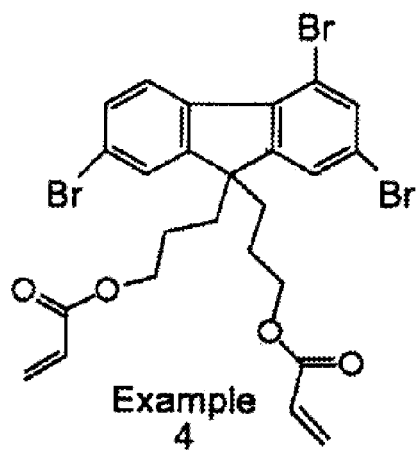
Figure 3:
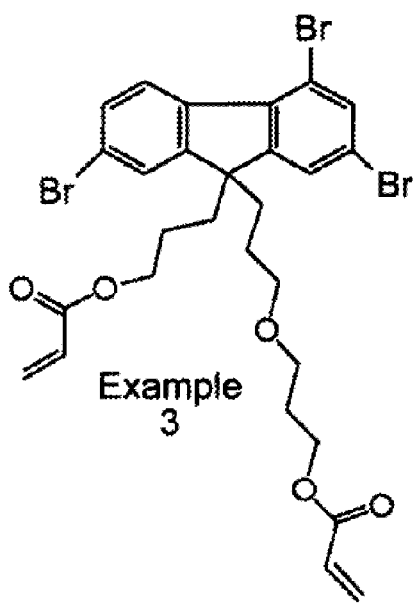
Figure 3:
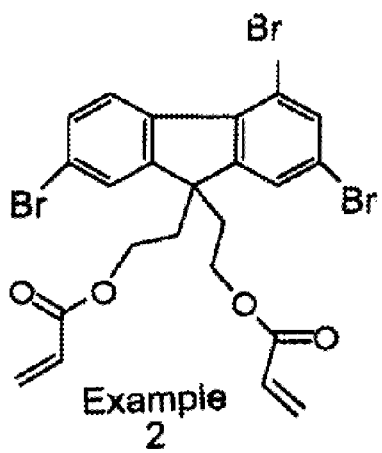
Figure 3:
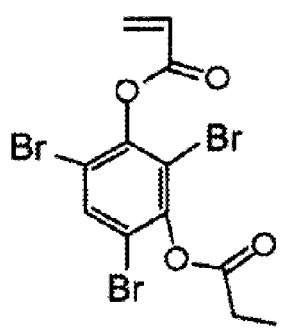

In yet another aspect of the invention, the optical films described above are included within an antireflective film construction. As shown in FIGS. 1 and 4, a coating 10, and preferably an antireflective coating, contains a substrate 12 formed from PET or polycarbonate, or any other material recognized for its utility as a substrate in antireflective films. An optional adhesive 14 may be provided on one side of the substrate 12 whereby the substrate 12 is coupled to a display device 16 and also to a juxtaposed layer outwardly oriented from the substrate 12. In accordance with the present invention, a hardcoat layer 18 is coupled to and layered over or otherwise fixed to substrate 12 in a known manner thereby forming an outwardly oriented layer in physical contact with substrate 12. An optical layer 20 having a relatively high refractive index of at least 1.6, formed as described above, is next coupled to and/or layered over hardcoat layer 18. If desired, the construct 10 may include other layers typically used in antireflective film such as a relatively lower refractive index layer 22, or an anti-smudge layer (not shown) as known in the art.

The low index layer 20 may be formed as known in the art. U.S. Pat. No. 6,723,423 exemplifies the known understanding of forming a low refractive index layer and is herein incorporated by reference, although not by way of limitation. An exemplary low index layer may be formed from low refractive index fluoropolymer compositions and derived from an interpenetrating polymer network or semi-interpenetrating polymer network which includes a reactive fluoroplastic and/or a fluoroelastomer (i.e. the functional fluoropolymer phase) blended with multi-functional acrylates (i.e. the acrylate phase) such as trimethylolpropane triacrylate (TMPTA) and optionally additional fluorinated mono-functional acrylates or multi-functional fluorinated acrylates which can be coated and cured by ultraviolet light or by thermal means. The presence of an acrylate crosslinker provides a composition with both low refractive index and improved adhesion to high index polymer substrates such as polyethylene terephthalate ("PET") or hard coated PET films. The low index coating mixture preferably describes a reactive high molecular weight fluoropolymer(s) that can participate in the crosslinking reactions between the monomeric multi-functional acrylates. This enhances the crosslinkability of the fluoropolymer phase to the forming polyacrylate phase and produces a co-crosslinked, interpenetrating or semi-interpenetrating polymer network with enhanced interfacial contact between the high index layer and the low index layer and thereby improves durability and low refractive index.

Various optional permanent and removable grade adhesive compositions 14 may be coated on the opposite side of the substrate 12 (i.e. to that of the hardcoat 18) so the article 10 can be easily mounted to a display surface. Typically, the adhesive 14, substrate 12, and hard coating layer 18 are prepackaged as a film 19 having a release layer (not shown) attached to the adhesive 14. The release layer is then removed and the adhesive layer 14 coupled to a housing or other area of the display 16 to form the optical display 16.

Suitable optional adhesive compositions 14 include (e.g. hydrogenated) block copolymers such as those commercially available from Kraton Polymers, Westhollow, Tex. under the trade designation "Kraton G-1657", as well as other (e.g. similar) thermoplastic rubbers. Other exemplary adhesives include acrylic-based, urethane-based, silicone-based and epoxy-based adhesives. Preferred adhesives are of sufficient optical quality and light stability such that the adhesive does not yellow with time or upon weather exposure so as to degrade the viewing quality of the optical display. The adhesive can be applied using a variety of known coating techniques such as transfer coating, knife coating, spin coating, die coating and the like. Exemplary adhesives are described in U.S. Patent Application Publication No. 2003/0012936, herein incorporated by reference. Several of such adhesives are commercially available from 3M Company, St. Paul, Minn. under the trade designations 8141, 8142, and 8161. The substrate layer 12 may consist of any of a wide variety of non-polymeric materials, such as glass, or polymeric materials, such as polyethylene terephthalate (PET), bisphenol A polycarbonate, cellulose triacetate, poly(methyl methacrylate), and biaxially oriented polypropylene which are commonly used in various optical devices.

It is contemplated that the present invention will find primary application in optical coatings and films including antireflective film, for example. However, it is not limited thereto. It will also be understood that the foregoing description of an embodiment of the present invention is for illustrative purposes only. As such, the various structural and operational features herein disclosed are susceptible to a number of modifications commensurate with the abilities of one of ordinary skill in the art, none of which departs from the scope of the present invention as defined in the appended claims.

What is claimed is:

1. A bromo-substituted fluorene monomer defined by either one of the following formulae:

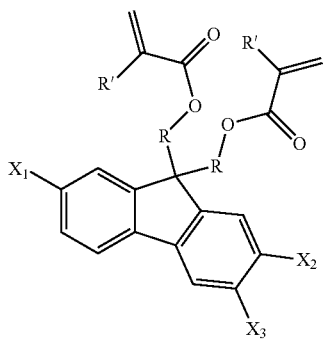

X1 = Br
X2 = H or Br
X3 = H or Br (only when X2 = Br)
R = alkylene or alkylene oxy (up to 8 atoms)
R' = H or methyl -continued

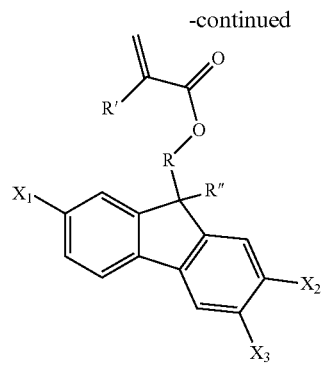

X1 = Br
X2 = H or Br
X3 = H or Br (only when X2 = Br)
R = alkylene or alkylene oxy (up to 8 atoms)
R' = H or methyl
R" = H or alkyl.

2. The monomer of claim 1 selected from the group consisting of acrylic acid 3-[9-(3-acryloyloxy-propyl)-2,3,7-tribromo-9H-fluoren-9-yl]-propyl ester, acrylic acid 3-{9-[3-acyloyloxy-propoxy)-propyl]-2,3,7-tribromo-9H-fluoren-9-yl}-propyl ester, 3-[9-(3-acryloyloxy-propyl)-2,7-dibromo-9H-fluoren-9-yl]-propyl ester, and 2-[9-(2-acryloyloxy-ethyl)-2,7-dibromo-9H-fluoren-9-yl]-ethyl ester.

3. A polymerizable composition comprising a bromo-substituted fluorene monomer defined by either one of the following formulae:

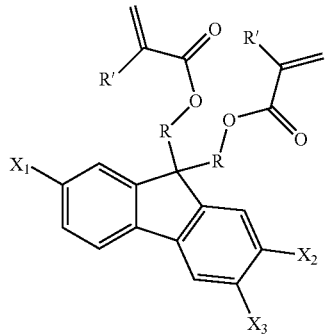

X1 = Br
X2 = H or Br
X3 = H or Br (only when X2 = Br)
R = alkylene or alkylene oxy (up to 8 atoms)
R' = H or methyl

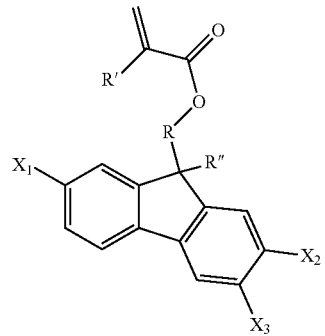

X1 = Br
X2 = H or Br
X3 = H or Br (only when X2 = Br)
R = alkylene or alkylene oxy (up to 8 atoms)
R' = H or methyl
R" = H or alkyl.

4. The composition of claim 3 wherein said bromo substituted fluorene monomer is selected from the group consisting of acrylic acid 3-[9-(3-acryloyloxy-propyl)-2,3,7-tribromo-9H-fluoren-9-yl]-propyl ester, acrylic acid 3-{9-[3-acyloyloxy-propoxy)-propyl]-2,3,7-tribromo-9H-fluoren-9-yl}-propyl ester, 3-[9-(3-acryloyloxy-propyl)-2,7-dibromo-9H-fluoren-9-yl]-propyl ester, and 2-[9-(2-acryloyloxy-ethyl)-2,7-dibromo-9H-fluoren-9-yl]-ethyl ester.

* * * * *

UNITED STATES PATENT AND TRADEMARK OFFICE
CERTIFICATE OF CORRECTION

PATENT NO. : 7,297,810 B2
APPLICATION NO. : 11/026674
DATED : November 20, 2007
INVENTOR(S) : Christopher B. Walker, Jr.

It is certified that error appears in the above-identified patent and that said Letters Patent is hereby corrected as shown below:

Column 6
Line 17, Delete "tetrahydopyranyl" and insert -- tetrahydropyranyl --, therefor.
Line 35, Delete "1;1" and insert -- 1:1 --, therefor.
Line 67, Delete "30" and insert -- 30° --, therefor.

Column 7
Line 1, Delete "30 C" and insert -- 30° C. --, therefor.
Line 29, Delete "50 C," and insert -- 50° C., --, therefor.
Line 30, Delete "35 C" and insert -- 35° C. --, therefor.

Column 8
Line 17-18, Delete "patent application No. US2003 0165680," and
insert -- Patent Application Publication No. 2003/0165680, --, therefor.

Column 11-12
Line 1, Before "Table" insert -- TABLE 6 --.
Line 7, Below "thickness" delete "apprx" and insert -- approx --, therefor.

UNITED STATES PATENT AND TRADEMARK OFFICE
CERTIFICATE OF CORRECTION

PATENT NO. : 7,297,810 B2  
APPLICATION NO. : 11/026674  
DATED : November 20, 2007  
INVENTOR(S) : Christopher B. Walker, Jr.

It is certified that error appears in the above-identified patent and that said Letters Patent is hereby corrected as shown below:

Column 11  
Line 27, Delete "Modifers" and insert -- Modifiers --, therefor.  
Line 30, Delete "methacrylaoxypropyltrimethoxy" and insert -- methacryloxypropyltrimethoxy --, therefor.  
Line 38, Delete "90C" and insert -- 90° C. --, therefor.  
Line 45, Delete "NH3" and insert -- $NH_3$ --, therefor.  
Line 46, Delete "4 l t" and insert -- 4 lt --, therefor.(Consider Space)  
Line 58, Delete "(363 g )" and insert -- (363 g) --, therefor. (Consider Space)

Signed and Sealed this

Twentieth Day of May, 2008

JON W. DUDAS  
*Director of the United States Patent and Trademark Office*

UNITED STATES PATENT AND TRADEMARK OFFICE
CERTIFICATE OF CORRECTION

PATENT NO.       : 7,297,810 B2
APPLICATION NO.  : 11/026674
DATED            : November 20, 2007
INVENTOR(S)      : Christopher B. Walker, Jr.

It is certified that error appears in the above-identified patent and that said Letters Patent is hereby corrected as shown below:

In the Drawings:
On Sheet 2 in Fig. 3, delete "Example 2" and insert --Example 4--.
On Sheet 2 in Fig. 3, delete "Example 4" and insert --Example 2--.
As shown in the attached.

Column 8:
Line 60, delete "DBFDC2A" and insert --TBFDA--.

Signed and Sealed this

Twentieth Day of January, 2009

JON W. DUDAS
*Director of the United States Patent and Trademark Office*

Example 1

Example 4

Example 3

Example 2

Comparative Example 1